United States Patent [19]

Huston et al.

[11] Patent Number: 5,132,405

[45] Date of Patent: * Jul. 21, 1992

[54] BIOSYNTHETIC ANTIBODY BINDING SITES

[75] Inventors: James S. Huston, Chestnut Hill; Hermann Oppermann, Medway, both of Mass.

[73] Assignee: Creative BioMolecules, Inc., Hopkinton, Mass.

[*] Notice: The portion of the term of this patent subsequent to Feb. 25, 2009 has been disclaimed.

[21] Appl. No.: 213,671

[22] Filed: Jun. 30, 1988

Related U.S. Application Data

[63] Continuation of Ser. No. 52,800, May 21, 1987.

[51] Int. Cl.$^5$ .................... C07K 15/28; C12N 5/10; C12N 5/20; C12P 21/08
[52] U.S. Cl. .................... 530/387.3; 424/85.8; 424/85.91; 435/69.1; 435/69.6; 435/70.21; 435/172.2; 435/172.3; 435/240.27; 435/252.3; 435/320.1; 530/388.26; 935/15; 536/27
[58] Field of Search .............. 424/85.8, 85.91; 435/68.1, 69.1, 69.4, 69.6, 69.7, 70.1, 70.21, 172.1, 172.2, 172.3, 240.27, 252.3, 252.33, 320.1; 436/542; 530/350, 380, 387–389, 399; 536/27; 935/15, 72, 73

[56] References Cited

U.S. PATENT DOCUMENTS

| | | | |
|---|---|---|---|
| 4,474,893 | 10/1984 | Reading | 436/547 |
| 4,642,334 | 2/1987 | Zaffaroni et al. | 530/388 |
| 4,666,837 | 5/1987 | Harford et al. | 435/68 |
| 4,704,692 | 11/1987 | Ladner | 364/496 |
| 4,946,778 | 8/1990 | Ladner et al. | 435/69.6 |

FOREIGN PATENT DOCUMENTS

| | | |
|---|---|---|
| 0088994 | 9/1983 | European Pat. Off. . |
| 120694 | 10/1984 | European Pat. Off. . |
| 843023680 | 11/1984 | European Pat. Off. . |
| 183964 | 10/1985 | European Pat. Off. . |
| 184187A | 12/1985 | European Pat. Off. . |
| 851026658 | 2/1986 | European Pat. Off. . |
| 853056042 | 3/1986 | European Pat. Off. . |
| 205326A | 6/1986 | European Pat. Off. . |
| 861024073 | 9/1986 | European Pat. Off. . |
| 8601533 | 3/1976 | PCT Int'l Appl. . |
| 8600090 | 6/1984 | PCT Int'l Appl. . |
| 8801775 | 6/1984 | PCT Int'l Appl. . |
| 8801649 | 9/1986 | PCT Int'l Appl. . |
| 2137631 | 3/1984 | United Kingdom . |
| 2188638 | 10/1987 | United Kingdom . |
| 8702671 | 5/1987 | World Int. Prop. O. . |

OTHER PUBLICATIONS

Jones et al., "Replacing the Complementarity-Determining Regions in a Human Antibody With Those From a Mouse," *Nature*, 321:522-525, May 29, 1986.
Van Brunt (1986) Biotechnology, 4:277-283.
Wetzel et al. (1981) Gene, 16:63-71.
Cabilly et al. (1984) Proc. Natl. Acad. Sci. USA, 81:3273-3277.

(List continued on next page.)

*Primary Examiner*—John Doll
*Assistant Examiner*—Robert D. Budens
*Attorney, Agent, or Firm*—Testa, Hurwitz & Thibeault

[57] ABSTRACT

Disclosed are a family of synthetic proteins having affinity for a preselected antigen. The proteins are characterized by one or more sequences of amino acids constituting a region which behaves as a biosynthetic antibody binding site (BABS). The sites comprise 1) non-covalently associated or disulfide bonded synthetic $V_H$ and $V_L$ dimers, 2) $V_H$-$V_L$ or $V_L$-$V_H$ single chains wherein the $V_H$ and $V_L$ are attached by a polypeptide linker, or 3) individual $V_H$ or $V_L$ domains. The binding domains comprise linked CDR and FR regions, which may be derived from separate immunoglobulins. The proteins may also include other polypeptide sequences which function e.g., as an enzyme, toxin, binding site, or site of attachment to an immobilization media or radioactive atom. Methods are disclosed for producing the proteins, for designing BABS having any specificity that can be elicited by in vivo generation of antibody, and for producing analogs thereof.

4 Claims, 22 Drawing Sheets

OTHER PUBLICATIONS

Vogel (1987) Current Approaches of Immunotargeting In Immunoconjugates Antibody Conjugates in Radioimaging and Therapy of Cancer (C.-W. Vogel, ed.) N.Y., Oxford University Press, pp. 3–7.
Itakura et al. (1977) Science, 198:1056–1063.
Hochman et al., Biochemistry 12:1130–1138.
Schultz, P. G., Science 240:426–432 (1988).
Abstract A; Blue Sheets 5:S5 (Jul. 3, 1985).
Letter from Mr. Joseloff (NIH).
Abstract B (Jan. 27, 1986) SBIR Phase I.
SBIR (NIH) Phase II Grant Application (Dec. 13, 1985).
Brown et al. Cancer Res. 47:3577.
Gascoigne et al., PNAS (USA) 84:2936.
Tan et al., J. Immunol. 135:3564.
Takeda et al., Nature (London) 314:453.
Kabat et al., PNAS (USA) 75:2429.
Tonegawa et al., PNAS (USA) 74:3518.
Nishimura et al., Cancer Res. 47:999.
Morrison, Science (WDC) 229:1202.
Boulianne et al., Mol. Biol. Med. (ENG) 4:37.
Liu et al., Gene (Neth) 54:33.
Baer et al., Cell 43:705.
Corvalen et al. (1987) Cancer Immunol. Immunother. 24:133–137.
Corvalen and Smith (1987) Cancer Immunol. Immunother. 24:127–132.
Sun et al., (1987) Proc. Natl. Acad. Sci. USA 84:214–218.
Boulianne et al., (1984) Nature 312:543–646.
Haber and Novotny (1985) "The Antibody Combining Site" in Hybridoma Technology in the Bioscience and Medicine, Plenum Publishing Corp. pp. 57–76.
Haber (1983) Biochem. Pharmacol. 32:1967–1977.
Marx (1985) Science 229:455–456.
Kabat et al. (1979) Sequence of Immunoglobulin Chains.
NIH Publication No. 80-2008, pp. 1–107.
Morrison et al., (1984) Proc. Natl. Acad. Sci. USA 81:6851–6855.
Neuberger et al., (1984) Nature 312:604–608.
Rice and Baltimore (1982) Proc. Natl. Acad. Sci. USA, 79:7862–7865.
Rosemblatt and Haber (1978) Biochem. 17:3877–3882.
Erlich et al. (1980) Biochem. 19:4091–4096.
Inbar et al. (1972) Proc. Natl. Acad. Sci. USA 69:2659–2662.
Sharon and Givol (1976) Biochem. 15:1591–1594.
Huston et al. (1972) Biochem. 11:4256–4262.
Dammacco et al. (1972) J. Immunol. 109:565–569.
Sahagan et al. (1986) J. Immunol. 137:1066–1074.
"Genex makes a miniaturized monoclonal antibody", Newswatch, Monday, Oct. 20, 1986, p. 5.
Klausner (1986) Biotechnol. 4:1041–1043.

FIG. 1B 26-10 GENES/PROTEINS

V_H: FR1 | CDR1 | FR2 | CDR2 | FR3 | CDR3 | FR4

- AMINO ACID SEQUENCE NO.: 31 35 — 50 64 — 100 106 119
- DNA BASE NO.: 93 115 — 150 192 — 300 318 357

V_L: FR1 | CDR1 | FR2 | CDR2 | FR3 | CDR3 | FR4

- AMINO ACID SEQUENCE NO.: 24 37 — 55 61 — 90 101 113
- DNA BASE NO.: 72 111 — 165 183 — 288 303 339

```
g-loop:
QVQLQQSGPELVEPGASVRISCTASGYTFTNYYIHWLKQRPGQGLEWIGVIYPGNGNTK
YNENFKGKATLTADKSSSTAFNQISSLTSEDSAVYFCARYTHYYF  DYWGQGTTLTVSSK*

26-10:
EVQLQQSGPELVKPGASVRMSCKSSGYIFTDFYMNWVRQSHGKSLDYIGYISPYSGVTG
YNQKFKGKATLTVDKSSSTAYMELRSLTSEDSAVYYCAGSSGNKVAMDYVWGHGASVTVSS*

26-10/g-loop hybrid:
EVQLQQSGPELVKPGASVRMSCKSSGYtftnyyihwlkQSHGKSLewigwIypgngntkynenfkgK
                           (cdr1-----)          (cdr2-----------------)
                              hphI    bstXI    xbaI                draI
ATLTaDKSSSTAYMELRSLTSECSAVYYCArythyyf  DYWGHGASVTVSS*
- -)                    (cdr3-----)
     hincII          sacII           nheI newm/g-loop hybrid:
EVQLQQSGPGLVRPSQTLSLTCTVSGStftnyyihwlkQPPGRGLewigwIypğngntkynenfkg
              [newm1...........]            [newm2..]
                 avaII.........hphI            bstXI...xbaI
                                                         narI
RVTMLVDTSKNQFSLRLSSVTAADTAVYYCArythyyf  DVWGQGSLVTVSS*
  [newm3................................]          [newm4]
     draI........................sacII         ..............

newm:
EVQLQQSGPGLVRPSQTLSLTCTVSGSTFSNDYYTWVRQPPGRGLEWIGYVFYHGTSDDTTP
LRS RVTMLVDTSKNQFSLRLSSVTAADTAVYYCARNLIAGCIDVWGQGSLVTVSS*
```

FIG. 3

```
         10        20        30        40        50        60        70
GAATTCGAAGTTCAACTGCAGCAGTCTGGTCCTGAATTGGTTAAACCTGGGCCCTCTGTGCGCATGTCCT
GluPheGluValGlnLeuGlnSerGlyProGluLeuValLysProGlyAlaSerValArgMetSerC
AsuII       BbvI  AvaII                       AhaII       HhaI
EcoRI       Fnu4HI Sau96I                     BanI        HinPI
  TaqI        PstI                      EcoRII           MstINlaIII
                                              HaeII      FspI
                                              HhaI
                                              HinPI
                                              NarI
                                              NlaIV
                                              ScrFI
                                              AcyI 80        90        100       110       120       130       140
GCAAATCCTCTGGTACATTTCACCGACTTCTACATGAATTGGGTTCGCCAGTCTCATGGTAAGTCTCT
ysLysSerSerGlyTyrIlePheThrAspPheTyrMetAsnTrpValArgGlnSerHisGlyLysSerLe
          RsaI  HphI                     NlaIII           BstXI NlaIII   Xba
                                                                         Ma 150       160       170       180       190       200       210
AGACTACATCGGGTACATTCCCCATACTCTGGGGTTACCGGTACAACCAGAAGTTAAAGGTAAGGCG
uAspTyrIleGlyTyrIleSerProTyrSerGlyValThrGlyTyrAsnGlnLysPheLysGlyLysAla
I         RsaI                              BstEII                     DraI
eI                                            HpaII
                                              MaeIII
```

FIG. 4A.1

```
          220       230       240       250       260       270       280
ACCCTTACTGTCGACAAATCTTCCTCAACTGCTTACATGGAGCTGCGTTCTTTGACCTCTGAGGACTCCG
ThrLeuThrValAspLysSerSerThrAlaTyrMetGluLeuArgSerLeuThrSerGluAspSerA
AccI     MboII                 AluI                         DdeI HinfIFn
HincII                          NlaIIIBbvI                            Sac
SalI                                   Fnu4HI
TaqI 290       300       310       320       330       340       350
CGGTATACTATTGCCGCGGCTCCTCTGGTAACAAATGGGCCATGGATTACTGGGGTCATGGCGCCTCTGT
laValTyrTyrCysAlaGlySerGlyAsnLysTrpAlaMetAspTyrTrpGlyHisGlyAlaSerVa
uDII       HhaIBanII        HaeIII                         AhaII      Ma
IIAccI     FnuDII            NcoI                           BanI
           HinPINlaIV        NlaIII                         HaeII
                             Sau96I                         HhaI
                             StyI                           HinPI
                                                            NarI
                                                            NlaIII
                                                            NlaIV
                                                            AcyI 360       370
TACTGTATCCTCATAGGATCC
lThrValSerSer*amAsp
eIII      BamH1
          NlaIV
          Sau3A
          XhoII
```

FIG. 4A.2

```
         10        20        30        40        50        60        70
GAATTCGACGTCGTAATGACCCAGACTCCGCTGTCTCTGCCGGTTTCTCTGGGTGACCAGGCTTCTATTT
GluPheAspValValMetThrGlnThrProLeuSerLeuProValSerLeuGlyAspGlnAlaSerIle
EcoRI AatII                    HinfI         HpaII         BstEII
      AhaI                                                 HphI EcoRII
  TaqI                                                          ScrFI
  AcyI                                                      MaeIII
   MaeII 80        90       100       110       120       130       140
CTTGCCGCTCTTCCCAGTCTCTGGTCTCCATTCTAATGGTAACACTTACCTGAACTGGTACCTGCAAAAGGC
erCysArgSerGlnSerLeuValHisSerAsnGlyAsnThrTyrLeuAsnTrpTyrLeuGlnLysAl
Fnu4HI       AvaII           MaeIII        HgiEII    BanI
      MboII     BstXI                                    KpnI
             Sau96I                                       NlaIV
                                                           RsaI
```

FIG. 4B.1

```
        150         160         170         180         190         200         210
TGGTCAGTCTCTCCGAAGCTTCTGATCTACAAAGTCTCTACAACCGCTTCTCTCTGGTGTCCCGGATCGTTTCTCT
aGlyGlnSerSerProLysLeuLeuIleTyrLysValSerAsnArgPheSerLeuValSerArgPheSerGlyValProAspArgPheSer
             AluI    Sau3A                                              HpaII
             HindIII                                                     NciISau3A
                                                                         ScrFI 220         230         240         250         260         270         280
GGTTCTGGTTCTGGTACTGACTTCACCCTGAAGATCTCTCGTGTCGAGGCCGAGGATCTGGGTATCTACT
GlySerGlySerGlyThrAspPheThrLeuLysIleSerArgValGluAlaGluAspLeuGlyIleTyrP
     RsaI     HphI       BglII              TaqIHaeIII Sau3A
               MboII                                   XhoII
               Sau3A
               XhoII 290         300         310         320         330         340         350
TCTGCTCTCAGACTACTCATGTACCGCCCGACCTTCGGCGGTGGCACCAAGCTCGAGATCAAAACGTTGAGGATCC
heCysSerGlnThrThrHisValProProThrPheGlyGlyGlyThrLysLeuGluIleLysArg*op
    DdeI    NlaIII        HgiEII    BanI  AluI   Sau3A MaeII      BamHI
            RsaI                    NlaIV AvaI                    NlaIV
                                          TaqI                    Sau3A
                                          XhoI                    XhoII
```

FIG. 4B.2

```
          10                 20                 30                 40                 50                 60                 70
GAATTCGAAGTTCAACTGCAGCAGTCTCTGGTCTTCCTGAATTGGTTAAACCTGGCCGCCCTCTGTGCCATGTCCT
GluPheGluValGlnLeuGlnSerGlyProGluLeuValLysProGlyAlaSerValArgMetSerC
EcoRI AsuII   BbvI   AvaII                   AhaII          HhaI
      TaqI   Fnu4HI  Sau96I                  BanI           HinPI
             PstI                            EcoRII         MstNlaIII
                                                            FspI
                                             HaeII
                                             HhaI
                                             HinPI
                                             NarI
                                             NlaIV
                                             AcyI 80                 90                100                110                120                130                140
GCAAATCCTCTGGGTACATTTCACCATTACTACATCCATTGGGTTCGCCAGTCTCATGGTAAGTCTCT
                                           CATGTAAAAGTGGTTAATGATGTAGGTAACCCAAGCGGTC
ysLysSerSerGlyTyrIlePheThrAsnTyrTyrIleHisTrpValArgGlnSerHisGlyLysSerLe
      RsaI  HphI              FokI                     BstXI  NlaIII   Xba
                                                                       Ma 150                160                170                180                190                200                210
AGACTACATCGGGTGGATCTACCCCGGGATCTAATGGTAACACTAAGTACTACAATGAGAACTTTAAAGGTAAG
                                                                    TGATGTCTCCCACCTAGATGGGCCCATTACCATTGTGATTCATGATGTTACTCTTGAAA
uAspTyrIleGlyTrpIleTyrProGlyIleAsnGlyAsnThrLysTyrTyrAsnGluAsnPheLysGlyLys
      Sau3A AvaI  HpaII       MaeIIIDdeIRsaI
I     XhoII       NcII        ScaI                                  DraI
e                 NcII
                  SmaI
                  XmaI
```

FIG. 4C.1

```
         220        230        240        250        260        270        280
GCCGACCCTTACTGTCGACAAATCTTCCTCAACTGCTTACATGGAGCTGCGTTCTTTGACCTCTGAGGACT
AlaThrLeuThrValAspLysSerSerThrAlaTyrMetGluLeuArgSerLeuThrSerGluAspS
         AccI      MboII              AluI                        DdeI HinfI
         HincII                        NlaIII BbvI
         SalI                                 Fnu4HI
         TaqI 290        300        310        320        330        340        350
CCGCGGTATACTATTGCGCGGGCCTCCTCTGGTAACAAATGGGCCTTCGATTACTGGGGTCATGGGCCCTC
erAlaValTyrTyrCysAlaGlySerSerGlyAsnLysTrpAlaPheAspTyrTrpGlyHisGlyAlaSe
I         AccI      HhaIBanII         MaeIII          GGAAGCTAATGACCCCAGTACCGC
FnuDII    FnuDII              HaeIII                  AhaII
SacII              HinPINlaIV         Sau96ITaqI      BanI
                                                      HaeII    HhaI
                                                               HinPI
                                                               NarI
                                                               NlaIII
                                                                   NlaIV
                                                                   AcyI 360        370
TGTTACTGTATCCTCATAGGATCC
rValThrValSerSer*am
MaeIII   BamHI
         NlaIV
         Sau3A
         XhoII
```

FIG. 4C.2

```
                      10                  20                  30                  40                  50                  60                  70
         GAATTCGACGTCGTAATGACCCAGAGACTCCGCTGTCTCTGCCGGTTTCTCTGGGTGACCAGGCTTCTATTT
         GluPheAspValValMetThrGlnThrProLeuSerLeuProValSerLeuGlyAspGlnAlaSerIleS
         EcoRI AatII                          HinfI                HpaII        BstEII
               AhaII                                                    HphI EcoRII
               TaqI                                                         ScrFI
               AcyI                                                         MaeIII
               MaeII 80                  90                 100                 110                 120                 130                 140
         CTTGCCGCTCTTCCCAGTCTATTGTGCACTCTAATGGTAACACTTACCTGGATTGGTACCTGCAAAAGGC
         AACGGCGAGAAGGGTCAGATAACACGTGAGATTACCATTGTGAATGGACCTAAC
         erCysArgSerGlnSerIleValHisSerAsnGlyAsnThrTyrLeuAspTrpTyrLeuGlnLysAl
         Fnu4HI                  HgiAI            MaeIII            EcoRII     BanI
                MboII                                                    ScrFI   KpnI
                                                                         HgiEII  NlaIV
                                                                                  RsaI 150                 160                 170                 180                 190                 200                 210
         TGGTCAGTCTCCGAAGCTTCGATCTCACAAAGTCTCTAACCGCTTCTCTGGTGTCCCGGATCGTTTCTCT
         aGlyGlnSerProLysLeuLeuIleTyrLysValSerAsnArgPheSerGlyValProAspArgPheSer
                        AluI  Sau3A                                      HpaII
                              HindIII                                    NciISau3A
                                                                              ScrFI
```

FIG. 4D.1

```
         220       230       240       250       260       270       280
GGTTCTGGTTCTGGTACTGACTTCACCCTGAAGATCTCTCGTGTCGAGGCCGAGGATCTGGGTATCTACT
GlySerGlySerGlyThrAspPheThrLeuLysIleSerArgValGluAlaGluAspLeuGlyIleTyrT
         Rsa I     HphI    BglI I            TaqIHaeIII Sau3A
                           MboII                    XhoII
                           Sau3A
                           XhoII

GGCTCCTAGACCCATAGATGA 290       300       310       320       330       340       350
ACTGCTTCCAGGGGTCTCTCATGTACCGTGGACCTTCGGCGGTGGACCAAGCTCGAGATCAAACGTTGAGGATCC
TGACGAAGGTCCCCAGAGTACATGGCACCTGGAAGCCGCCACCCTGGTTCGAGCT
yrCysPheGlnGlySerHisValProTrpThrPheGlyGlyGlyGlyThrLysLeuGluIleLysArg*op
    EcoRII  NlaIII  Ava II  BanI  AluI  Sau3A MaeII     BamHI
    ScrFI   RsaI    Sau96I  NlaIV       AvaI            NlaIV
                    HgiEII              TaqI            Sau3A
                                        XhoI            XhoII
```

FIG. 4D.2

```
         10              20              30              40              50              60              70
GAATTCATGGAAGTACAACAATCTGGGCCCGGTCTGGTACCTCCGTCTCAGACTCTGTCCCTGA
GluPheMetGluValGlnLeuGlnLeuGlnlnSerGlyProGlyLeuValArgProSerGlnThrLeuSerLeuT
EcoRINlaIII RsaI      ApaIHpaII  RsaI    MaeII  DdeIHinfI
                      BanII                     Tth111I
                      HaeIII
                      NciI
                      NlaIV
                      Sau96I
                      ScrFI 80              90             100             110             120             130             140
CTTGTACCGTATCCGGATCCACCTTCTCTAACTACTACATCCATTGGGTCCGTCAACCGCCGGGTCGTGG
hrCysThrValSerGlySerThrPheSerAsnTyrTyrIleHisTrpValArgGlnProProGlyArgGl
RsaI         BamH1              FokI        AvaIIHincII  HpaII
             HpaII                           NlaIV        NciI
             NlaIV                           Sau96I       ScrFI
             Sau3A
             XhoII 150             160             170             180             190             200             210
TCTCGAGTGGATCGGTTGGATTTACCCGGGTAATGGTAACACTAAGTACTACAATGAGAACTTTAAAGGC
yLeuGluTrpIleGlyTrpIleTyrProGlyAsnGlyAsnThrLysTyrTyrAsnGluAsnPheLysGly
AvaI    Sau3A  AvaI     HpaII         HaeIIIDdeIRsaI              DraI    N
TaqI           HpaII    NciI                ScaI                          Sp
XhoI           NciI     ScrFI
               ScrFI    SmaI
                        XmaI
```

FIG. 4E.1

```
       220        230        240        250        260        270        280
ATGCTGGTCGACACTTCTAAGAACCAATTCTCTCTGCGTCTTCTGTTACCCGGCTGATACTGCTG
MetLeuValAspThrSerLysAsnGlnPheSerLeuArgLeuLeuSerValThrAlaAlaAspThrAlaV
laIII AccI      DdeIXmnI         HgaI MboII MaeIIIFnu4HI
hI    HincII                          BbvII      FnuDII
      SalI                                       SacII
      TaqI 290        300        310        320        330        340        350
TGTACTACTGCGCCGCGTTCCTCCGGTAATAAGTGGGCATTTGATTACTGGGGCCAGGGCTCTCTGGTCAC
alTyrTyrCysAlaArgSerSerGlyAsnLysTrpAlaPheAspTyrTrpGlyGlnGlySerLeuValTh
RsaI  BssHII     HpaII                         NlaIV BanII     BstEII
      FnuDII                                         EcoRII     HphI
      FnuDII                                         HaeIII     MaeIII
      HhaI                                           Sau96I
      HinPI                                          ScrFI
      HinPI 360        370
CGTATCCTCTTAACTGCAG
rValSerSer*ocLeuGln
         PstI
```

FIG. 4E.2

```
         10        20        30        40        50        60        70
GAATTCATGGAATCTGTTCTGACTCAGCCGCCTCTGTATCTGGTGCACCGGGTCAACGCGGTAACTATCT
GluPheMetGluSerValLeuThrGlnProProSerValSerGlyAlaProGlyGlnArgValThrIleS
EcoRI    HinfI    DdeIFnu4HI              HglAIHpaII         FnuDII
     NlaIII           HinfI                     NciIHincII MaeIII
     XmnI                                          ScrFI   MluI 80        90       100       110       120       130       140
CTTGCCGTTCCTCTCAGTCTATTGTCCATTCTAATGGCAACACTTATCTGGAATGGTACCAACAACTGCC
erCysArgSerSerGlnSerIleValHisSerAsnGlyAsnThrTyrLeuGluTrpTyrGlnGlnLeuPr
        DdeI        BstXI                            BanI              Hp
                                                     KpnI              Nc
                                                     NlaIV             Sc
                                                     RsaI 150       160       170       180       190       200       210
GGGCACCGGCGCCCGAAGCTGCTGATCTTTAAAGTATCTAATCGCTTCTCTGGCGTACCGGATCGATTCT
oGlyThrAlaProLysLeuLeuIlePheLysValSerAsnArgPheSerGlyValProAspArgPheSer
aII  FnuDII AluI   DraI                        RsaI    ClaI
iI   HhaI   BbvI Sau3A                               HpaII HinfI
rFI  HinPI  Fnu4HI                                        Sau3A
BanI                                                          TaqI
NlaIV
```

FIG. 4F.1

```
          220         230         240         250         260         270         280
GTATCTAAGTCTCTGGCTCCTCTGCCACTCTGCCGATCACTGGTCTGCAAGCAGAAGATGAGGCCGATTACT
ValSerLysSerGlySerAlaThrLeuAlaIleThrGlyLeuGlnAlaGluAspGluAlaAspTyrT
DdeI    NlaIV   BglI           Sau3A                MboII     HaeIII 290         300         310         320         330         340         350
ACTGTTTTCAAGGCTCTCATGTACCGTGGACCTTCGGTGGTGGCACCAAGCTTACTGTACTGCGTCAGCC
yrCysPheGlnGlySerHisValProTrpThrPheGlyGlyGlyThrLysLeuThrValLeuArgGlnPr
          NlaIII    AvaII               BanI     AluI     RsaI HgaI
          RsaI      Sau96I               NlaIV   HindIII
                    HgiEII 360
GTAACTGCAG
o*ocLeuGln
PstI
HaeIII
```

FIG. 4F.2

```
                                                                                              FR-1
     10         20        30        40        50        60        70
GAAGTTCAACTGCAGCAGTCTGGTCCTGAATTGGTTAAACCTGGCCCTCTGTGCGATGTCCTGCAAATCCTCA
 E  V  Q  L  Q  Q  S  G  P  E  L  V  K  P  G  A  S  V  R  M  S  C  K  S  S
          BbvI+           AvaII              AhaII          HhaI       MnlI+
          Fnu4HI          Sau96I             BanIMnlI+      HinPI
          PstI                                EcoRII        FspINlIII
                                                HaeII       NspHI
                                                HhaI
                                                HinPI
                                                NarI
                                                NlaIV
                                                ScrFI

X1              FR-2                         X2
     85        95        105       115       125       135       145
GGGTACCGCCAGTCTCCATGGTAAGTCTTAAGTCTCTAGAGCTTTAAAGGCGACTTTAAAGGTAAGGCCGACCCTTACTGTCGACAAATCTTCCTCA
 G  Y  R  Q  S  H  G  K  S  L  D  F  K  G  K  A  T  L  T  V  D  K  S  S  S
 BanI    NlaIII         XbaI                                    AcoI     MboII
 KpnI    BstXI                                                  HincII   MnlI-
 NlaIV                                 DraI                     SalI
 RsaI                                                           TaqI
```

FIG. 5.1

```
         FR-3
         160         170         180         190         200                    210              220
ACTGCTTACATGGAGCTGCGTTCTTTGACCTCTGAGGACTCCGCGGTATACTATTGCGCGGGTATCGATTATTGG
 T  A  Y  M  E  L  R  S  L  T  S  E  D  S  A  V  Y  Y  C  A  R  I  D  Y  W
         AluI        DdeI HinfI       AccI              AccII ClaI
        NlaIII BbvI-  MnlI+MnlI-      AccII             AccII   TaqI
              Fnu4HI                  NspBII            BssHII
                                      SacI              HhaI
                                                        HinPI
                                                        HinPI FR-4
    235        245         255         265
GGCCATGGCGCTAGCGTTACCGTGAGCTCCTAAGGATCC
 G  H  G  A  S  V  T  V  S  S  *  G  S
aIV    HaeII    AluI DdeIBamHI
au96I  HhaI     BanII MstII NlaIV
HaeIII HinPI    Bsp1286    Sau3A
NcoI   NheI     HgiAI      XhoII
NlaIII          SacI
StyI
```

FIG. 5.2

```
     E   F   M   A   D   N   K   F   N   K   E   Q   Q   N   A   F   Y   E   I   L   M   L   P   N   L
EcoRINlaIII                                                   AccII           BglII                BspMI+
                                                              AflIII          Sau3A
                                                              MluI
         85          95         105         115         125         135         145
AACGAAGAGCAGCGTAACGGCTTCATCCAAAGCTTGAAAGACGACCCGTCTCAGAGACGGCTAACCTGCTGGCAGAG
  N   E   Q   R   N   G   F   I   Q   S   L   K   D   D   P   S   Q   S   A   N   L   L   A   E   H
      BbvI+              FokI-       AluI                  DdeI HaeII         BsPMI+              MnlI
      Fnu4HI                         HindIII                    Eco47III
                                                                HhaI
MboII+                                                          HinPI
        160         170         180         190         200         210         220
GCCAAGAAACTGAACGACGCTCAGGCGCCGAAGAGTGATCCCGAAGTTCAACTGCAGCAGTCTGGTCCTGAATTG
  A   K   K   L   N   D   A   Q   A   P   K   S   D   P   E   V   Q   L   Q   Q   S   G   P   E   L
               DdeIAhaII   MboII+ Sau3A                     BbvI+           AvaII
HgaI+          BanI                                         Fnu4HI          Sau96I
               HaeII                                        PstI
               HhaI
               HinPI
               NarI
               NlaIV
        235         245         255         265         275         285         295
GTTAAACCTGGGCGCCTCTGTGCGCATGTCCTGCAAATCCTCTGGGTACATTTTCACCGACTTCTACATGAATTGG
  V   K   P   G   A   S   V   R   M   S   C   K   S   S   G   Y   I   F   T   D   F   Y   M   N   W
         AhaII     HhaI        MnlI+ RsaI             HphI-         NlaIII
         BanIMnlI+ HinPI
         EcoRII  FspINlaIII
                  HaeII  NspHI
           HhaI
           HinPI
           NarI
           NlaIV
           ScrFI
```

FIG. 6-1

```
              310       320       330       340       350       360       370
         GTTCGCCAGTCTCATGGTAAGTCTCTAGACTACATCGGGTACATTCCCCATACTCTGGGGTTACCGGCTACAA
          V  R  Q  S  H  G  K  S  L  D  Y  I  G  Y  I  S  P  Y  S  G  V  T  G  Y  N
            BstXI  NlaIII       XbaI              RsaI           PflMI       BstEII
                                                                              Cfr10I
                                                                              HpaII 385       395       405       415       425       435       445
         CAGAAGTTTAAAGGTAAGGCCGACCCTTACTGTCGACAAATCTTCCTCAACTGCTTACATGGAGCTGCTTCTTTG
          Q  K  F  K  G  K  A  T  L  T  V  D  K  S  S  S  T  A  Y  M  E  L  R  S  L
              DraI                      AccI        MboII-            AluI
                                        HincII      MnlI+             NlaIIIBbvI-
                                        SalI                               Fnu4H1
                                        TaqI 460       470       480       490       500       510       520
         ACCTCTGAGGACTCCCGGGTATACTATTGCGCGGGCTCCTCTGGTAACAAATGGGCCATGGATTATTGGGGTCAT
          T  S  E  D  S  A  V  Y  Y  C  A  G  S  S  G  N  K  W  A  M  D  Y  W  G  H
          DdeI HinfI  AccI              AccI   MnlI+           HaeIII           Nla
          MnlI+MnlI-  AccII              HhaIBanII              NcoI             NlaIII
                      NspBII              Bsp1286                Sau96I
                      SacII               HinPINlaIV                 StyI 535       545       555       565       575       585       595
         GGTGCTAGCGTTACTGTGAGCTTCTGGTGGCCGGTGGGCCTCGGGTGGCCTGCGGGATCCGGACGTC
          G  A  S  V  T  V  S  S  G  G  G  G  S  G  G  G  G  S  G  G  G  G  S  D  V
          IIINheI    AluI                                                    BamHI AatII
                     BanII                                          AvaI  Fnu4HISau3AAhaII
                     Bsp1286                                                    NlaIV
                     HglAI
                     SacI
```

FIG. 6-2

```
          610         620         630         640         650         660         670
GTTGTTACCCAGACTCCGGCTCTGTCTCTGCCGGTTTCTCTGGGTGACCAGGCTTCTATTTCTTGCCGCTTCCCAG
 V  V  T  Q  T  P  L  S  L  P  V  S  L  G  D  Q  A  S  I  S  C  R  S  S  Q
              HinfI       Cfr10I    BstEII         Fnu4HI     PflM
                 NspBII    HpaII    HphI+EcoRII               MboII-
                                            ScrFI 685         695         705         715         725         735         745
TCTCTGGTCCATTCTAATGGTAACACTTACCTGAACTGGTACCTGCAAAAGGCTGGTCAGTCTCCGAAGCTTCTG
 S  L  V  H  S  N  G  N  T  Y  L  N  W  Y  L  Q  K  A  G  Q  S  P  K  L  L  S
 I  AvaII                             BanI                              AluI
    BstXI                              BspMI+                           HindIII
    Sau96I                             KpnI
                                       NlaIV
                                       RsaI 760         770         780         790         800         810         820
ATCTACAAAGTCTCTAACCGCTTCTCTGGTGTCCCGGATCGTTTCTCTGGTTCTGGTTCTGGTACTGACTTCACC
 I  Y  K  V  S  N  R  F  S  G  V  P  D  R  F  S  G  S  G  S  G  T  D  F  T
au3A                          HpaII
                              NciISau3A
                              ScrFI 835         845         855         865         875         885         895
CTGAAGATCTCTCGTGTCGAGGCCGAAGACCTGGGTATCTACTTCTGCTCTCAGACTACTCATGTACCGCCGACT
 L  K  I  S  R  V  E  A  E  D  L  G  I  Y  F  C  S  Q  T  T  H  V  P  P  T
    BglII    TaqIHaeIII    EcoRII            DdeI          NlaIII
    MboII+       MnlI- MboII-                              RsaI
    Sau3A                 ScrFI 910         920         930         940
TTTGGTGGTGGCACCAAGCTCGAGATTAAACGTTAACTGCAG
 F  G  G  G  T  K  L  E  I  K  R  *  L  Q
   BanI  AluI           HincII
   NlaIV AvaI           HpaI PstI
         TaqI
```

FIG. 6-3

BIOSYNTHETIC ANTIBODY BINDING SITES

The United States government has rights in this invention pursuant to small business innovation research grant number SSS-4 1 R43 CA39870-01 and SSS-4 2 R44 CA39870-02. This application is a continuation of copending application Ser. No. 052,800 filed May 21, 1987.

REFERENCE TO RELATED APPLICATIONS

This application is a continuation of copending application Ser. No. 052,800 filed May 21, 1987. Related applications include: Ser. Nos. 636,770 and 636,765, both filed Jan. 2, 1991, which are divisions of Ser. No. 213,761 filed June 30, 1988, which also is a continuation of 052,800, Ser. No. 342,449, filed Feb. 6, 1989, which is a continuation-in-part of 052,800.

BACKGROUND OF THE INVENTION

This invention relates to novel compositions of matter, hereinafter called biosynthetic antibody binding sites or BABS, useful, for example, in specific binding assays, affinity purification, biocatalysis, drug targetinq, imaging, immunological treatment of various oncogenic and infectious diseases, and in other contexts. More particularly, this invention relates to biosynthetic polypeptides having a structure similar to native antibody binding sites, DNAs encoding the polypeptides Prepared by recombinant DNA techniques, vectors comprising these DNAs, and methods for the design and production of these polypeptides.

Antibodies are Proteins belonging to a group of immunoglobulins elicited by the immune system in response to a specific antigen or substance which the body deems foreign. Antibodies can both recognize and bind that antigen, and are involved in a number of effector reactions such as complement fixation and allergic responses.

There are five classes of human antibodies which have the ability to selectively recognize and preferentially bind a specific antigen. Each antibody class has the same basic structure (see FIG. 1), or multiples thereof, consisting of two identical polypeptides called heavy or H chains (molecular weight in IgG approximately 50,000 d each) and two identical polypeptides called light or L chains (molecular weight approximately 25,000 d each). Each of the five antibody classes has a similar set of light chains and a distinct set of heavy chains. A light chain is composed of one variable and one constant domain, while a heavy chain is composed of one variable and three or more constant domains. The variable domains determine the specificity of the immunoglobulin, the constant regions have other functions.

Amino acid sequence data indicate that each variable domain comprises three hypervariable regions flanked by four relatively conserved framework regions (Kabat et. al., *Sequences of Proteins of Immunological Interest* [U.S. Department of Health and Human Services, third edition 1983, fourth edition, 1987]). The hypervariable regions have been assumed to be responsible for the binding specificity of individual antibodies and to account for the diversity of binding of antibodies as a protein class.

Monoclonal antibodies, or homogeneous antibodies of identical genetic parentage and binding specificity, have been useful both as diagnostic and therapeutic agents. They are routinely produced according to established procedures by hybridomas generated by fusion of mouse lymphoid cells with an appropriate mouse myeloma cell line. Human monoclonal antibodies are difficult to produce by cell fusion techniques since, among other Problems, human hybridomas are notably unstable, and removal of immunized spleen cells from humans is not feasible as it is for rodents. Monoclonals which have specificities of significant therapeutic value are generally of murine or rat origin, and are therefore immunogenic to the human immune system.

Chimeric antibodies composed of human and non-human amino acid sequences potentially have improved therapeutic value as they presumably would elicit less circulating human antibody against the non-human immunoglobulin sequences. Accordingly, hybrid antibody molecules have been proposed which consist of immunoglobulin light and heavy chain amino acid sequences from different mammalian sources. The chimeric antibodies designed thus far comprise variable regions from one mammalian source, and constant regions from human or another mammalian source (Morrison et al., 1984, Proc. Natl. Acad. Sci. U.S.A., 81:5851–6855; Neuberger et al., 1984, Nature 312:604–608; Sahagan et al., 1986, J. Immunol. 137:1066–1074; EPO application nos. 84302368.0, Genentech; 85102665.8, Research Development Corporation of Japan; 85305604.2, Stanford; P.C.T. application no. PCT/GB85/00392, Celltech Limited).

It has been reported that constant regions are not required for antigen recognition or binding; these properties have been localized to the variable domains of the antibody molecule located at the amino terminal end of both the heavy and light chains. The variable regions remain noncovalently associated (as $V_H$ $V_L$ dimers, termed Fv regions) even after proteolytic cleavage from the native antibody molecule, and retain much of their antigen recognition and bindinq capabilities (Inbar et al., Proc. Natl. Acad. Sci. U.S.A., 1972, 69:2659–2662; Hochman et. al., 1973, Biochem. 12:1130–1135 and 1976, Biochem. 15:2706–2710; Sharon and Givol, 1976, Biochem. 15:1591–1594; Rosenblatt and Haber, 1978, Biochem. 17:3877–3882; Ehrlich et al., 1980, Biochem. 19:4091–40996).

SUMMARY OF THE INVENTION

A class of novel biosynthetic polypeptides has now been designed and engineered which comprise biosynthetic antibody binding sites, that is, "BABS" or chimeric polypeptides defining structure capable of selective antigen recognition and preferential antigen binding.

In its broadest aspects, this invention features polypeptides comprising biosynthetic antibody binding sites, DNA encoding these polypeptides prepared by recombinant DNA techniques, vectors comprising these DNAs, and methods for the production of these polypeptides.

In one aspect, the invention is based on the observation that three subregions of the variable domain of each of the heavy and light chains of native immunoglobulin molecules collectively are responsible for antigen recognition and binding. Each of these subregions, called herein "complementarity determining regions" or CDRs, consists of one of the hypervariable regions or loops and of selected amino acids or amino acid sequences disposed in the framework regions which flank that Particular hypervariable region. It has now been discovered that framework regions from diverse species are effective to maintain CDRs from diverse other species in proper conformation so as to achieve true immunochemical binding properties in a biosynthetic protein. Thus, BABS produced in accordance with the invention comprise biosynthetically produced novel sequences of amino acids defining polypeptides designed to bind with a preselected antigenic material. The structure of these synthetic polypeptides is unlike that of naturally occurring antibodies, fragments thereof, or known synthetic polypeptides or "chimeric antibodies" in that the regions of the BABS responsible for specificity and affinity of binding, (analogous to native antibody variable regions) are themselves chimeric, e.g., comprise amino acid sequences homologous to portions of at least two different antibody molecules.

The invention thus provides a chimeric polypeptide defining a region capable of selective antigen binding and recognition. This chimeric polypeptide comprises amino acid sequences homologous to portions of the CDRs of the variable domain of one immunoglobulin light or heavy chain, and other sequences homologous to the framework regions, or FRs, of the variable domain of a second, different immunoglobulin light or heavy chain. Polypeptides so constructed bind a specific preselected antigen determined by the CDRs. Preferably, the chimeric polypeptides comprise an amino acid sequence homologous to at least a portion of the variable regions of a mammalian immunoglobulin, such as those of mouse, rat, or human origin. In one preferred embodiment, the biosynthetic antibody binding site comprises FRs homologous with a portion of the FRs of a human immunoglobulin and CDRs homologous with CDRs from a mouse immunoglobulin. This type of chimeric polypeptide displays the antigen binding specificity of the mouse immunoglobulin, while its human framework minimizes human immune reactions. In addition, the chimeric polypeptide may comprise other amino acid sequences. It may comprise, for example, a sequence homologous to a portion of the constant domain of an immunoglobulin, but preferably is free of constant regions (other than FRs).

The invention also provides a single chain composite polypeptide having antigen binding abilities, and comprising a pair of amino acid sequences homologous or analogous respectively to the variable regions of an immunoglobulin light and heavy chain, (linked $V_H$-$V_L$ or single chain Fv). Both $V_H$ and $V_L$ may copy natural monoclonal sequences, or one or both of the chains may comprise a CDR-FR construct of the type described above. The separate polypeptides analogous to the variable regions of the light and heavy chains are held together by a polypeptide linker.

This type of chimeric polypeptide is thus a single chain composite polypeptide comprising a complete antibody binding site. This single chain composite polypeptide has a structure patterned after tandem $V_H$ and $V_L$ domains, but with the carboxyl terminal of one attached through an amino acid sequence to the amino terminal of the other. It thus comprises an amino acid sequence which is homologous to a portion of the variable region of an immunoglobulin heavy chain ($V_H$) peptide bonded to a second amino acid sequence which is homologous to a portion of the variable region of an immunoglobulin light chain ($V_L$). The linking amino acid sequence may or may not itself be antigenic or biologically active. In addition, either the amino or carboxyl terminal ends of these chimeric, single chain Fvs may be attached to an amino acid sequence which itself is bioactive to produce a bifunctional or multifunctional protein. For example, the synthetic Fv may include a leader or trailer sequence defining a polypeptide having enzymatic activity, independent affinity for an antigen different from the antigen to which the chimeric Fv is directed, or having other functions such as to provide a convenient site of attachment for a radioactive atom, or simply to enhance expression in procaryotic host cells or Yeasts.

Such tandem arrangement of $V_H$ and $V_L$ polypeptides can increase the stability of the antigen binding site and facilitate its coupling to proteins utilized in drug targeting and moieties useful in imaging. The therapeutic use of such chimeric Fvs provide a number of advantages over larger fragments or complete antibody molecules: they are often quite stable and less immunogenic; they can penetrate body tissues more rapidly for purposes of imaging or drug delivery because of their smaller size; and they can facilitate accelerated clearance of targeted isotopes or drugs.

Other embodiments of the invention comprise multifunctional polypeptides consisting of one or more single chain Fvs either linked $V_H$ and $V_L$ dimers, individual $V_L$ or $V_H$, or any of the foregoing comprising CDRs and FRs from different or the same immunoglobulins, linked to a second functional protein domain such as, for example, a toxin, enzyme, or site of attachment to an immobilization matrix. Yet another embodiment is a polypeptide comprising several identical or non-identical BABS which recognize a group of antigenic determinants that are periodic or closely spaced in their normal environment, e.g., on a cell surface. This arrangement confers greatly augmented affinity and/or specificity on the BABS-containing protein analogous to, for example, the way IgM (containing 10 Fabs) binds to the surfaces of certain cells.

In other aspects, the invention provides DNA sequences encoding chimeric polypeptides of the type described above, vectors including such sequences, and methods employing the DNAs and vectors for producing the polypeptides.

A novel method of producing BABS involves the construction of a DNA containing three polynucleotide sequences ($X_1$, $X_2$ and $X_3$) Each of the sequences contain restriction sites proximal its 3' and 5' ends, and each is flanked by polynucleotide sequences ($FR_1$, $FR_2$, $FR_3$ and $FR_4$) encoding selected framework region (FR) amino acid sequences homologous to a portion of the variable domain of an immunoglobulin. This DNA has the structure:

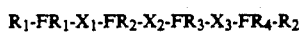

$R_1$-$FR_1$-$X_1$-$FR_2$-$X_2$-$FR_3$-$X_3$-$FR_4$-$R_2$ where $R_1$ is a 5' phosphate group or polynucleotide sequence and $R_2$ is a 3' hydroxyl group or polynucleotide sequence. The X polynucleotide sequences may be selectively excised using restriction enzymes and replaced by other DNA sequences encoding the CDR amino acid sequences of a variable domain of a selected immunoglobulin. This type of DNA sequence may encode at least part of the variable region of either or both a heavy or light chain of an immunoglobulin and may, in addition, comprise a third phosphodiester-linked nucleotide or polynucleotide sequence of a nature and function described above.

In yet another aspect, the invention provides a method for producing intact biosynthetic antibody binding sites or native Fv free of all or substantially all constant region amino acids. The method involves enzymatic digestion of chimeric immunoglobulin or at least Fab regions which have been engineered to contain preferential proteolytic cleavage sites located between the variable and constant regions of the immunoglobulin heavy and light chains. Digestion of the intact immunoglobulin with the appropriate protease yields a complete antigen binding site or Fv fragment. This approach works well in myeloma or hybridoma expression systems.

Accordingly, it is an object of this invention to provide novel proteins comprising biosynthetic antibody binding sites including an amino acid sequence homologous to specific portions of the variable region of immunoglobulin light chain and/or heavy chain, to provide DNA sequences which encode the biosynthetic antibody binding sites, and to provide replicable expression vectors capable of expressing DNA sequences encoding the biosynthetic antibody binding sites. Another object is to provide a generalized method for producing biosynthetic antibody binding site polypeptides of any desired specificity.

BRIEF DESCRIPTION OF THE DRAWING

The foregoing and other objects of this invention, the various features thereof, as well as the invention itself, may be more fully understood from the following description, when read together with the accompanying drawings.

FIG. 1B is a schematic drawing of the structure of Fv illustrating $V_H$ and $V_L$ domains, each of which comprises four framework (FR) regions and three complementarity determining regions (CDR). Boundaries of CDRs are indicated, by way of example, for monoclonal 26-10, a well known and characterized murine monoclonal specific for digoxin.

FIG. 3 discloses five amino acid sequences (heavy chains) in single letter code lined up vertically to facilitate understanding of the invention. Sequence 1 is the known native sequence of $V_H$ from murine monoclonal glp-4 (anti-lysozyme). Sequence 2 is the known native sequence of $V_H$ from murine monoclonal 26-10 (anti-digoxin). Sequence 3 is a BABS comprising the FRs from 26-10 $V_H$ and the CDRs from glp-4 $V_H$. The CDRs are identified in lower case letters; restriction sites in the DNA used to produce chimeric sequence 3 are also identified. Sequence 4 is the known native sequence of $V_H$ from human myeloma antibody NEWM. Sequence 5 is a BABS comprising the FRs from NEWM $V_H$ and the CDRs from glp-4 $V_H$, i.e., illustrates a binding site having a human framework but an affinity for lysozyme similar to glp-4.

FIGS. 4A –4F are the synthetic nucleic acid sequences and encoded amino acid sequences of (4A) the heavy chain variable domain of mouse anti-digoxin monoclonal 26-10; (4B) the light chain variable domain of mouse anti-digoxin monoclonal 26-10; (4C) a heavy chain variable domain of a chimeric Fv (BABS) comprising CDRs of glp-4 and FRs of 26-10; (4D) a light chain of the same BABS; (4E) a heavy chain variable region of a BABS comprising CDRs of glp-4 and FRs of NEWM; and (4F) a light chain variable region comprising CDRs of glp-4 and FRS of NEWM. Delineated are FRs, CDRs, and restriction sites for endonuclease digestion, most of which were introduced during design of the DNA.

FIG. 5 is the nucleic acid and encoded amino acid sequence of a host DNA ($V_H$) designed to facilitate insertion of CDRs of choice. The DNA was designed to have unique 6-base sites directly flanking the CDRs so that relatively small oligonucleotides defining portions of CDRs can be readily inserted, and to have other sites to facilitate manipulations of the DNA to optimize binding properties in a given construct. The framework regions of the molecule correspond to mouse FRs (c.f. FIG. 4A).

FIG. 6 is a protein constructed in accordance with the invention comprising FB-Asp-Pro-$V_H$-(Gly$_4$-Ser)$_3$-$V'_L$. FB is the FB fragment of Protein A, here used as a leader, and constituting a binding site for Fc, Asp-Pro is a dilute acid cleavage site, and the remainder of the sequence comprises a single chain BABS comprising the $V_H$ and $V'_L$ chains of mouse monoclonal 26-10 linked together with a 15 amino acid sequence. $V'_L$ is the $V_L$ of mouse monoclonal 26-10 altered at residue 4 where valine replaces methionine. This construct binds both Fc and digoxin.

In FIGS. 4A-4E and 6, the amino acid sequence of the expression products start after the GAATTC sequences, which codes for an EcoRI splice site, translated as Glu-Phe on the drawings.

DESCRIPTION OF THE INVENTION

Figure 1A:
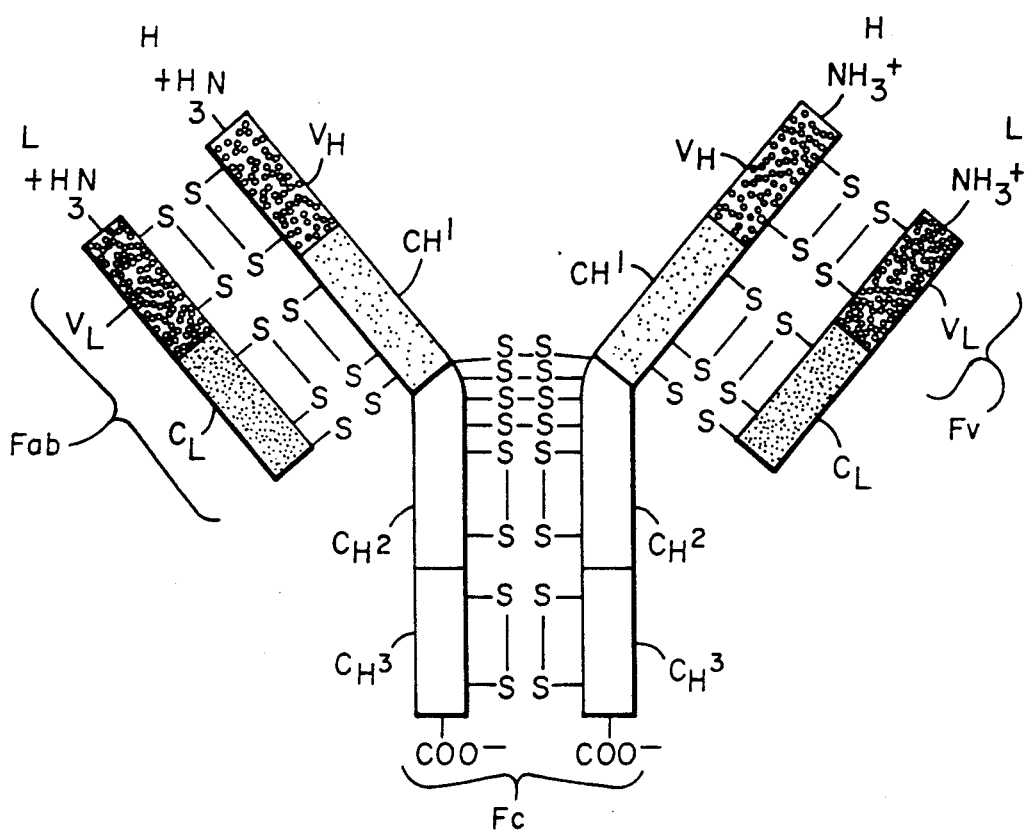
FIG. 1A is a schematic representation of an intact IgG antibody molecule containing two light chains, each consisting of one variable and one constant domain, and two heavy chains, each consisting of one variable and three constant domains.

As is now well known, Fv, the minimum antibody fragment which contains a complete antigen recognition and binding site, consists of a dimer of one heavy and one light chain variable domain in tight, noncovalent association (FIG. 1). It is in this configuration that the three complementarity determining regions of each variable domain interact to define an antigen binding site on the surface of the $V_H$-$V_L$ dimer. Collectively, the six complementarity determining regions (see FIG. 1B) confer antigen binding specificity to the antibody. FRs flanking the CDRs have a tertiary structure which is essentially conserved in native immunoglobulins of species as diverse as human and mouse. These FRs serve to hold the CDRs in their appropriate orientation. The constant domains are not required for binding function, but may aid in stabilizing $V_H$-$V_L$ interaction. Even a single variable domain (or half of an Fv comprising only three CDRs specific for an antigen) has the ability to recognize and bind antigen, although at a lower affinity than an entire binding site (Painter et al., 1972, Biochem. 11: 1327–1337).

This knowledge of the structure of immunoglobulin proteins has now been exploited to develop biosynthetic antibody binding sites provided by this invention.

The biosynthetic antibody binding sites embodying the invention are biosynthetic in the sense that they are synthesized in a cellular host made to express a synthetic DNA, that is, a recombinant DNA made from ligation of plural, chemically synthesized oligonucleotides, or by ligation of fragments of DNA derived from the genome of a hybridoma, mature B cell clone, or a cDNA library derived from such natural sources. The proteins of the invention are properly characterized as "antibody binding sites" in that these synthetic molecules are designed specifically to have at least some affinity for a preselected antigenic substance. The polypeptides of the invention are antibody-like in that their structure is patterned after regions of native antibodies known to be responsible for antigen recognition.

More specifically, the structure of these biosynthetic proteins in the region which impart the binding properties to the protein, is analogous to the Fv region of a natural antibody. It comprises a series of regions consisting of amino acids defining at least three polypeptide segments which together form the tertiary molecular structure responsible for affinity and binding. These regions are herein called complementarity determining regions or CDRs. These CDR regions are held in appropriate conformation by polypeptide segments analogous to the framework regions of the Fv fragment of natural antibodies.

The term CDR, as used herein, refers to amino acid sequences which together define the binding affinity and specificity of the natural Fv region of a native immunoglobulin binding site, or a synthetic Polypeptide which mimics this function. CDRs typically are not wholly homologous to hypervariable regions of natural Fvs, but rather also include specific amino acids or amino acid sequences which flank the hypervariable region and have heretofore been considered framework not directly determinitive of complementarity. The term FR, as used herein, refers to amino acid sequences interposed between CDRs.

The CDR and FR polypeptide segments are designed empirically based on sequence analysis of the Fv region of Preexisting antibodies or of the DNA encoding them. In one embodiment, the amino acid sequences constituting the FR regions of the BABS are analogous to the FR sequences of a first preexisting antibody, for example, a human IgG. The amino acid sequences constituting the CDR regions are analogous to the sequences from a second, different preexisting antibody, for example, the CDRs of a murine IgG. Alternatively, the CDRs and FRs from a single Preexisting antibody from, e.g., an unstable or hard to culture hybridoma, may be copied in their entirety.

Practice of the invention enables the design and biosynthesis of various reagents, all of which are characterized by a region having affinity for a preselected antigenic substance. Other regions of the biosynthetic protein are designed with the Particular Planned utility of the protein in mind. Thus, if the reagent is designed for intravascular use in mammals, the FR regions comprise amino acids similar or identical to at least a portion of the framework region amino acids of antibodies native to that mammalian species. On the other hand, the amino acids comprising the CDRs may be analogous to a portion of the amino acids from the hypervariable region (and certain flanking amino acids) of an antibody having a known affinity and specificity, e.g., a murine or rat monoclonal antibody.

Other sections, e.g., $C_H$ and $C_L$, of native immunoglobulin protein structure need not be present and normally are intentionally omitted from the biosynthetic Proteins of this invention. However the BABS of the invention may comprise additional polypeptide regions defining a bioactive region, e.g., a toxin or enzyme, or a site onto which a toxin or a remotely detectable substance can be attached.

The clinical administration of the BABS of the invention, which display the activity of native, relatively small Fv, $V_H$, or $V_L$ fragments, affords a number of advantages over the use of larger fragments or entire antibody molecules. The BABS of this invention offer fewer cleavage sites to circulating proteolytic enzymes and thus offer greater stability. They reach their target tissue more rapidly, and are cleared more quickly from the body. They also have reduced immunogenicity. In addition, their smaller size facilitates coupling to other molecules in drug targeting and imaging application.

The invention thus provides intact biosynthetic antibody binding sites analogous to $V_H$-$V_L$ dimers, either non-covalently associated, disulfide bonded, or linked by a polypeptide sequence to form a composite $V_H$-$V_L$ or $V_L$-$V_H$ polypeptide which is essentially free of the remainder of the antibody molecule. The invention also provides proteins analogous to an independent $V_H$ or $V_L$ domain. Any of these proteins may be provided in a form linked to amino acid sequences exclusive of those of the variable domain, for example, to amino acids analogous or homologous to Proteins of a constant domain, or another bioactive molecules such as a hormone or toxin. A proteolytic cleavage site can also be designed into the region separating the variable region-like sequences from other pendant sequences so as to facilitate cleavage of intact $V_H$ and/or $V_L$, free of other protein.

Figure 2A:
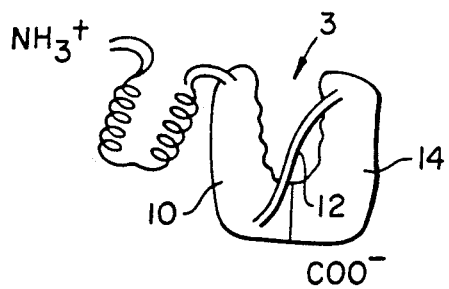
FIG. 2A-2D are schematic representations of some of the classes of reagents constructed in accordance with the invention, each of which comprises a biosynthetic antibody binding site.

FIGS. 2A, 2B, 2C, and 2D illustrate four examples of protein structures embodying the invention that can be produced by following the teaching disclosed herein. All are characterized by one or two biosynthetic polypeptide segments defining a binding site 3, and comprising amino acid sequences comprising CDRs and FRs, often derived from different immunoglobulins, or sequences homologous to a portion of CDRs and FRs from different immunoglobulins. FIG. 2A depicts a single chain Fv comprising a polypeptide 10 having an amino acid sequence analogous to the variable region of an immunoglobulin heavy chain, bound through its carboxyl end to a polypeptide linker 12, which in turn is bound to a polypeptide 14 having an amino acid sequence analogous to the variable region of an immunoglobulin light chain. Of course, the light and heavy chain domains may be in reverse order. The linker 12 should be at least long enough (e.g., about 15 amino acids or about 40A) to permit the chains 10 and 14 to assume their proper conformation. The linker 12 may comprise an amino acid sequence homologous to a sequence identified as "self" by the species into which it will be introduced, if drug use is intended. Unstructured, hydrophilic amino acid sequences are preferred. It may also comprise a bioactive polypeptide such as a cell toxin which is to be targeted by the binding site, or a segment easily labeled by a radioactive reagent which is to be delivered, e.g., to the site of a tumor comprising an epitope recognized by the binding site. Other proteins or polypeptides may be attached to either the amino or carboxyl terminus of protein of the type illustrated in FIG. 2A. As an example, a helically coiled polypeptide structure illustrating a leader comprising a protein A fragment is shown extending from the amino terminal end of $V_H$ domain 10.

Figure 2B:
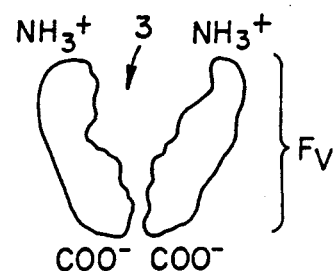
Figure 2C:
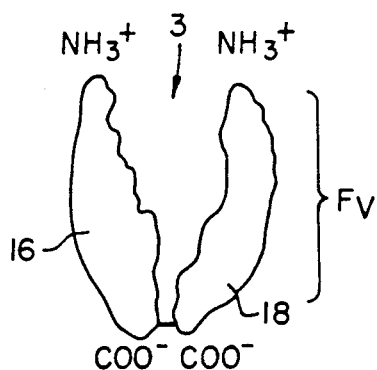

FIG. 2B illustrates two separate chains non-covalently associated and defining a binding site 3. It comprises separate peptides 16 and 18 comprising a chimeric $V_H$ and $V_L$ of the type described above. The carboxyl terminus of each protein chain may be designed to include one or more cysteine residues so that oxidation of properly folded structures produces disulfide bonds (see FIG. 2C) further stabilizing the BABS. Either or both of the polypeptides may further comprise a fused protein imparting other biological properties to the reagent in addition to the ability to bind to the antigen as specified by the interaction of the triplet CDRs on the respective polypeptides 16 and 18.

Figure 2D:
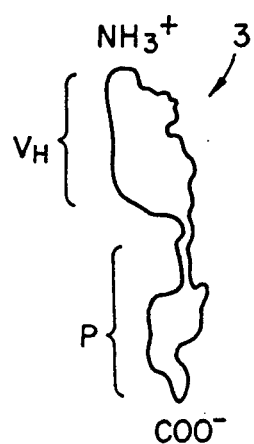

FIG. 2D depicts another type of reagent, comprising only one set of three CDRs, e.g., analogous to a heavy chain variable region, which retains a measure of affinity for the antigen. Attached to the carboxyl end of the polypeptide comprising the FR and CDR sequences constituting the binding site 3 is a pendant protein P consisting of, for example, a toxin, therapeutic drug, binding protein, enzyme or enzyme fragment, site of attachment for an imaging agent (e.g., to chelate a radioactive ion such as Indium), or site of attachment to an immobilization matrix so that the BABS can be used in affinity chromatography.

Of course, the protein may comprise more than one binding site or copies of a single binding site, and a number of other functional regions.

As is evidenced from the foregoing, the invention provides a large family of reagents comprising proteins, at least a portion of which defines a binding site patterned after the variable region or regions of natural immunoglobulins. It will be apparent that the nature of any protein fragments linked to the BABS, and used for reagents embodying the invention, are essentially unlimited, the essence of the invention being the provision, either alone or linked in various ways to other proteins, of binding sites having specificities to any antigen desired.

The BABS of the invention are designed at the DNA level. The chimeric or synthetic DNAs are then expressed in a suitable host system, and the expressed proteins are collected and renatured if necessary.

The ability to design the BABS of the invention depends on the ability to determine the sequence of the amino acids in the variable region of monoclonal antibodies of interest, or the DNA encoding them. Hybridoma technology enables production of cell lines secreting antibody to essentially any desired substance that produces an immune response. RNA encoding the light and heavy chains of the immunoglobulin can then be obtained from the cytoplasm of the hybridoma, and the 5' end portion of the mRNA can be used to prepare the cDNA for subsequent sequencing, or the amino acid sequence of the hypervariable and flanking framework regions can be determined by amino acid sequencing of the H and L chains and their V region fragments. Such sequence analysis is now conducted routinely. This knowledge permits one to design synthetic genes encoding FR and CDR sequences which likely will bind the antigen. These synthetic genes are then prepared using known techniques, or using the technique disclosed below, and then inserted into a suitable host, expressed, and purified. Depending on the host cell, renaturation techniques may be required to attain proper conformation. The various proteins are then tested for binding ability, and one having appropriate affinity is selected for incorporation into a reagent of the type described above. If necessary, Point substitutions seeking to optimize binding may be made in the DNA using conventional casette mutagenesis or other protein engineering methodology.

Of course, the processes for manipulating, amplifying, and recombining DNA which encode amino acid sequences of interest are generally well known in the art, and therefore, not described in detail herein. Methods of identifying and isolating genes encoding antibodies of interest are well understood, and described in the patent and other literature. In general, the methods involve selecting genetic material coding for amino acids which define the CDRs and FRs of interest according to the genetic code.

Accordingly, the construction of DNAs encoding BABS as disclosed herein can be done using known techniques involving the use of various restriction enzymes which make sequence specific cuts in DNA to produce blunt ends or cohesive ends, DNA ligases, techniques enabling enzymatic addition of sticky ends to blunt-ended DNA, construction of synthetic DNAs by assembly of short or medium length oligonucleotides, cDNA synthesis techniques, and synthetic Probes for isolating immunoglobulin genes. Various promoter sequences and other regulatory DNA sequences used in achieving expression, and various types of host cells are also known and available. Conventional transfection techniques, and equally conventional techniques for cloning and subcloning DNA are useful in the Practice of this invention and known to those skilled in the art. Various types of vectors may be used such as plasmids and viruses including animal viruses and bacteriophages. The vectors may exploit various marker genes which impart to a successfully transfected cell a detectable phenotypic property that can be used to identify which of a family of clones has successfully incorporated the recombinant DNA of the vector.

One method for obtaining DNA encoding the BABS disclosed herein is by assembly of synthetic oligonucleotides produced in a conventional, automated, polynucleotide synthesizer followed by ligation with appropriate ligases. For example, overlapping, complementary DNA fragments comprising 15 bases may be synthesized semi manually using phosphoramidite chemistry, with end segments left unphosphorylated to prevent polymerization during ligation. One end of the synthetic DNA is left with a "sticky end" corresponding to the site of action of a particular restriction endonuclease, and the other end is left with an end corresponding to the site of action of another restriction endonuclease. Alternatively, this approach can be fully automated. The DNA encoding the BABS may be created by synthesizing longer single strand fragments (e.g., 50-100 nucleotides long) in, for example, a Biosearch oligonucleotide synthesizer, and then ligating the fragments.

Still another method of producing the BABS of the invention is to produce a synthetic DNA encoding a polypeptide comprising, e.g., human FRs, and intervening "dummy" CDRs, or amino acids having no function except to define suitably situated unique restriction sites. This synthetic DNA is then altered by DNA replacement, in which restriction and ligation is employed to insert synthetic oligonucleotides encoding CDRs defining a desired binding specificity in the proper location between the FRs.

This technique is dependent upon the ability to cleave a DNA corresponding in structure to a variable domain gene at specific sites flanking nucleotide sequences encoding CDRs. These restriction sites in some cases may be found in the native gene. Alternatively, non-native restriction sites may be engineered into the nucleotide sequence resulting in a synthetic gene with a different sequence of nucleotides than the native gene, but encoding the same variable region amino acids because of the degeneracy of the genetic code. The fragments resulting from endonuclease digestion, and comprising FR-encoding sequences, are then ligated to non-native CDR-encoding sequences to produce a synthetic variable domain gene with altered antigen binding specifity. Additional nucleotide sequences encoding, for example, constant region amino acids or a bioactive molecule may also be linked to the gene sequences to produce a bifunctional protein.

The expression of these synthetic DNA's can be achieved in both prokaryotic and eucaryotic systems via transfection with the appropriate vector. In *E. coli* and other microbial hosts, the synthetic genes can be expressed as fusion protein. Expression in eucaryotes can be accomplished by the transfection of DNA sequences encoding CDR and FR region amino acids into a myeloma or other type of cell line. By this strategy intact hybrid antibody molecules having hybrid Fv regions and various bioactive proteins including a biosynthetic binding domain may be produced. For fusion protein expressed in bacteria subsequent Proteolytic cleavage of the isolated $V_H$ and $V_L$ fusions can be performed to yield free $V_H$ and $V_L$, which can be renatured, and reassociated (or used separately) to obtain an intact biosynthetic, hybrid antibody binding site.

Heretofore, it has not been possible to cleave the heavy and light chain region to separate the variable and constant regions of an immunoglobulin so as to produce intact Fv, except in specific cases not of general utility. However, one method of Producing BABS in accordance with this invention is to redesign an immunoglobulin at the DNA level so as to alter its specificity and so as to incorporate a cleavage site and "hinge region" between the variable and constant regions of both the heavy and light chains. Such chimeric antibodies can be produced in transfectomas or the like and subsequently cleaved using a preselected endopeptidase. The engineering principles involved in these easily cleaved constructs are disclosed in detail in copending U.S. application Ser. No. 028,484 filed Mar. 20, 1987 by Huston et al.

The hinge region is a sequence of amino acids which serve to Promote efficient cleavage by a preselected cleavage agent at a preselected, built-in cleavage site. It is designed to promote cleavage preferentially at the cleavage site when the Polypeptide is treated with the cleavage agent in an appropriate environment.

The hinge can take many different forms. Its design involves selection of amino acid residues (and a DNA fragment encoding them) which impart to the region of the fused protein about the cleavage site an appropriate polarity, charge distribution, and stereochemistry which, in the aqueous environment where the cleavage takes place, efficiently exposes the cleavage site to the cleavage agent in preference to other potential cleavage sites that may be present in the polypeptide, and/or to improve the kinetics of the cleavage reaction. In specific cases, the amino acids of the hinge are selected and assembled in sequence based on their known properties, and then the fused polypeptide sequence is expressed, tested, and altered for empirical refinement.

The hinge region is free of cysteine. This enables the cleavage reaction to be conducted under conditions in which the protein assumes its tertiary conformation, and may be held in this conformation by intramolecular disulfide bonds. It has been discovered that in these conditions access of the protease to potential cleavage sites which may be present within the target protein is hindered. The hinge region may comprise an amino acid sequence which includes one or more proline residues. This allows formation of a substantially unfolded molecular segment. Aspartic acid, glutamic acid, arginine, lysine, serine, and threonine residues maximize ionic interactions and may be present in amounts and/or in sequence which renders the moiety comprising the hinge water soluble.

In the case of single chain Fv comprising fused H and L chains, the cleavage site preferably is immediately adjacent the Fv polypeptide and comprises one or a sequence of amino acids exclusive of any one or sequence found in the amino acid structure of the BABS. Where BABS $V_H$ and $V_L$ regions are on separate chains (i.e., see FIG. 1A), the cleavage sites may be either immediately adjacent their C-terminal ends, thereby releasing Fv dimer of $V_H$ and $V_L$ upon appropriate cleavage (i.e., to yield the species of FIG. 2B), or may follow pendant polypeptides with or without cysteine that yield, respective, the species of FIG. 2C or 2D upon digestion.

The cleavage site preferably is designed for cleavage by a specific selected agent. Endopeptidases are preferred, although non-enzymatic (chemical) cleavage agents may be used. Many useful cleavage agents, for instance, cyanogen bromide, dilute acid, trypsin, *Staphylococcus aureus* V-8 protease, post proline cleaving enzyme, blood coagulation Factor Xa, enterokinase, and renin, recognize and preferentially or exclusively cleave particular cleavage sites. One currently preferred cleavage agent is V-8 protease. The currently preferred cleavage site is a Glu residue. Other useful enzymes recognize multiple residues as a cleavage site, e.g., factor Xa (Ile-Glu-Gly-Arg) or enterokinase (Asp-Asp-Asp-Asp-LYs).

EXEMPLIFICATION

FRs from the heavy and light chain murine anti-digoxin monoclonal 26-10 (FIGS. 4A and 4B) were encoded on the same DNAs with CDRs from the murine anti-lysozyme monoclonal glp-4 heavy chain (FIG. 3 sequence 1) and light chain to produce heavy (FIG. 4C) and light (FIG. 4D) chain together defining a chimeric antibody binding site which is specific for lysozyme. Murine CDRs from both the heavy and light chains of monoclonal glp-4 were encoded on the same DNAs with FRs from the heavy and light chains of human myeloma antibody NEWM (FIGS. 4E and 4F). The resulting interspecies chimeric antibody binding domain has reduced immunogenicity in humans because of its human FRs, and has specificity for lysozyme because of its murine CDRs.

A synthetic DNA was designed to facilitate CDR insertions into a human heavy chain framework and to facilitate empirical refinement of the resulting chimeric amino acid sequence. This DNA is depicted in FIG. 5.

A synthetic, bifunctional Protein was also designed at the DNA level, expressed, purified, renatured, and shown to bind specifically with a preselected antigen (digoxin). The detailed primary structure of this construct is shown in FIG. 6; its tertiary structure is illustrated schematically in FIG. 2A.

Details of these experiments, and the design principles on which the invention is based, are set forth below.

I. GENE DESIGN AND EXPRESSION

With the help of a computer program and known variable region DNA sequences, synthetic $V_L$ and $V_H$ genes may be designed which encode native or near native FR and CDR amino acid sequences from an antibody molecule, each separated by unique restriction sites located as close to FR-CDR and CDR-FR borders as possible. Alternatively, genes may be designed which encode native FR sequences which are similar or identical to the FRs of an antibody molecule from a selected species, each separated by "dummy" CDR sequences containing strategically located restriction sites. These DNAs serve as starting materials for producing BABS, as the native or "dummy" CDR sequences may be excised and replaced with sequences encoding the CDR amino acids defining a selected binding site. Alternatively, one may design and directly synthesize native or near-native FR sequences from a first antibody molecule, and CDR sequences from a second antibody molecule. Any one of the $V_H$ and $V_L$ sequences described above may be linked together directly, either via an amino acids chain or linker connecting the C-terminus of one chain with the N-terminus of the other, or via C-terminal cysteine residues on each of the $V_H$ and $V_L$.

These genes, once synthesized, may be cloned with or without additional DNA sequences coding for, e.g., an antibody constant region, or a leader peptide which facilitates secretion or intracellular stability of a fusion polypeptide. The genes then can be expressed directly in an appropriate host cell, or can be further engineered before expression by the exchange of FR, CDR, or "dummy" CDR sequences with new sequences. This manipulation is facilitated by the presence of the restriction sites which have been engineered into the gene at the FR-CDR and CDR-FR borders.

FIG. 3 illustrates the general approach to designing a chimeric $V_H$; further details of exemplary designs at the DNA level are shown in FIGS. 4A–4F. FIG. 3, lines 1 and 2, show the amino acid sequences of the heavy chain variable region of the murine monoclonals glp-4 (anti-lysozyme) and 26-10 (anti-digoxin), including the four FR and three CDR sequences of each. Line 3 shows the sequence of a chimeric $V_H$ which comprises 26-10 FRs and glp-4 CDRs. As illustrated, the hybrid protein of line 3 is identical to the native protein of line 2, except that 1) the sequence TFTNYYIHWLK has replaced the sequence IFTDFYMNWVR, 2) EWIG-WIYPGNGNTKYNENFKG has replaced DYIGYIS-PYSGVTGYNQKFKG, 3) RYTHYYF has replaced GSSGNKWAM, and 4) A has replaced V as the sixth amino acid beyond CDR-2. These changes have the effect of changing the specificity of the 26-10 $V_H$ to mimic the specificity of glp-4. The Ala to Val single amino acid replacement within the relatively conserved framework region of 26-10 is an example of the replacement of an amino acid outside the hypervariable region made for the purpose of altering specificity by CDR replacement. Beneath sequence 3 of FIG. 3, the restriction sites in the DNA encoding the chimeric $V_H$ (see FIGS. 4A–4F) are shown which are disposed about the CDR-FR borders.

Lines 4 and 5 of FIG. 3 represent another construct. Line 4 is the full length $V_H$ of the human antibody NEWM. That human antibody may be made specific for lysozyme by CDR replacement as shown in line 5. Thus, for example, the segment TFTNYYIHWLK from glp-4 replaces TFSNDYYTWVR of NEWM, and its other CDRs are replaced as shown. This results in a $V_H$ comprising a human framework with mouse sequences determining specificity.

By sequencing any antibody, or obtaining the sequence from the literature, in view of this disclosure one skilled in the art can produce a BABS of any desired specificity comprising any desired framework region. Diagrams such as FIG. 3 comparing the amino acid sequence are valuable in suggesting which particular amino acids should be replaced to determine the desired complementarity. Expressed sequences may be tested for binding and empirically refined by exchanging selected amino acids in relatively conserved regions, based on observation of trends in amino acid sequence data and/or computer modeling techniques.

Significant flexibility in $V_H$ and $V_L$ design is possible because the amino acid sequences are determined at the DNA level, and the manipulation of DNA is now accomplished easily.

For example, the DNA sequence for mouse $V_H$ and $V_L$ 26-10 containing specific restriction sites flanking each of the three CDRs was designed with the aid of a commercially available computer program which performs combined reverse translation and restriction site searches ("RV.exe" by Compugene, Inc.). The known amino acid sequences for $V_H$ and $V_L$ 26-10 polypeptides were entered, and all potential DNA sequences which encode those peptides and all potential restriction sites were analyzed by the program. The program can, in addition, select DNA sequences encoding the peptide using only codons preferred by $E.$ $coli$ if this bacterium is to be host expression organism of choice. FIGS. 4A and 4B show an example of program output. The nucleic acid sequences of the synthetic gene and the corresponding amino acids are shown. Sites of restriction endonuclease cleavage are also indicated. The CDRs of these synthetic genes are underlined.

The DNA sequences for the synthetic 26-10 $V_H$ and $V_L$ are designed so that one or both of the restriction sites flanking each of the three CDRs are unique. A six base site (such as that recognized by Bsm I or BspM I) is preferred, but where six base sites are not possible, four or five base sites are used. These sites, if not already unique, are rendered unique within the gene by eliminating other occurrences within the gene without altering necessary amino acid sequences. Preferred cleavage sites are those that, once cleaved, yield fragments with sticky ends just outside of the boundary of the CDR within the framework. However, such ideal sites are only occasionally possible because the FR-CDR boundary is not an absolute one, and because the amino acid sequence of the FR may not permit a restriction site. In these cases, flanking sites in the FR which are more distant from the predicted boundary are selected.

FIG. 5 discloses the nucleotide and corresponding amino acid sequence (shown in standard single letter code) of a synthetic DNA comprising a master framework gene having the generic structure:

$$R_1\text{-}FR_1\text{-}X_1\text{-}FR_2\text{-}X_2\text{-}FR_3\text{-}X_3\text{-}FR_4\text{-}R_2$$

where $R_1$ and $R_2$ are blunt ends which are to be ligated into a vector and $X_1$, $X_2$, and $X_3$ are DNA sequences whose only function is to provide convenient restriction sites for CDR insertion. This particular DNA has mouse FR sequences and unique, 6-base restriction sites adjacent the FR borders so that nucleotide sequences encoding CDRs from a desired monoclonal can be inserted easily. Restriction endonuclease digestion sites are indicated with their abbreviations; enzymes of choice for CDR replacement are underscored. Digestion of the gene with the following restriction endonucleases results in 3' and 5' ends which can easily be matched up with and ligated to native or synthetic CDRs of desired specificity: KpnI and BstXI are used for ligation of $CDR_1$; XbaI and DraI for $CDR_2$; and BssHII and ClaI for $CDR_3$.

II. OLIGONUCLEOTIDE SYNTHESIS

The synthetic genes and DNA fragments designed as described above preferably are produced by assembly of chemically synthesized oligonucleotides. 15-100mer oligonucleotides may be synthesized on a Biosearch DNA Model 8600 Synthesizer, and purified by polyacrylamide gel electrophoresis (PAGE) in Tris-Borate-EDTA buffer (TBE). The DNA is then electroeluted from the gel. Overlapping oligomers may be phosphorylated by T4 polynucleotide kinase and ligated into larger blocks which may also be purified by PAGE.

III. CLONING OF SYNTHETIC OLIGONUCLEOTIDE

The blocks or the pairs of longer oligonucleotides may be cloned into E. coli using a suitable, e.g., pUC, cloning vector. Initially, this vector may be altered by single strand mutagenesis to eliminate residual six base altered sites For example, $V_H$ may be synthesized and cloned into pUC as five primary blocks spanning the following restriction sites: 1. EcoRI to first NarI site; 2. first NarI to XbaI; 3. XbaI to SalI; 4. SalI to NcoI; 5. NcoI to BamHI These cloned fragments may then be isolated and assembled in several three-fragment ligations and cloning steps into the pUC8 plasmid. Desired ligations selected by PAGE are then transformed into, for example, E. coli strain JM83, and plated onto LB Ampicillin +Xgal plates according to standard procedures. The gene sequence may be confirmed by supercoil sequencing after cloning, or after subcloning into M13 via the dideoxy method of Sanger.

IV. CDR EXCHANGE

Three CDRs (or alternatively, four FRs) can be replaced per or $V_H$ or $V_L$. In simple cases, this can be accomplished by cutting the shuttle pUC plasmid containing the respective genes at the two unique restriction sites flanking each CDR or FR, removing the excised sequence, and ligating the vector with a native nucleic acid sequence or a synthetic oligonucleotide encoding the desired CDR or FR. This three part procedure would have to be repeated three times for total CDR replacement and four times for total FR replacement. Alternatively, a synthetic nucleotide encoding two consecutive CDRs separated by the appropriate FR can be ligated to a pUC or other plasmid containing a gene whose corresponding CDRs and FR have been cleaved out. This procedure reduces the number of steps required to perform CDR and/or FR exchange

V. EXPRESSION OF PROTEINS

The engineered genes can be expressed in appropriate prokaryotic hosts such as various strains of E. coli, and in eucaryotic hosts such as Chinese hamster ovary cell, mouse myeloma, and human myeloma/transfectoma cells.

For example, if the gene is to be expressed in E coli. it may first be cloned into an expression vector. This is accomplished by positioning the engineered gene downstream from a promoter sequence such as Trp or Tac, and a gene coding for a leader peptide such as fragment B of protein A (FB). The resulting expressed fusion protein accumulates in refractile bodies in the cytoplasm of the cells, and may be harvested after disruption of the cells by French press or sonication. The refractile bodies are solubilized, and the expressed proteins refolded and cleaved by the methods already established for many other recombinant proteins.

If the engineered gene is to be expressed in myeloma cells, the conventional expression system for immunoglobulins, it is first inserted into an expression vector containing, for example, the Ig promoter, a secretion signal, immunoglobulin enhancers, and various introns. This plasmid may also contain sequences encoding all or part of a constant region, enabling an entire part of a heavy or light chain to be expressed. The gene is transfected into myeloma cells via established electroporation or protoplast fusion methods. Cells so transfected can express $V_L$ or $V_H$ fragments, $V_L$-$V_H$ heterodimers, $V_H$-$V_L$ or $V_L$-$V_H$ single chain polypeptides, complete heavy or light immunoglobulin chains, or portions thereof, each of which may be attached in the various ways discussed above to a protein domain having another function (e.g., cytotoxicity).

Vectors containing a heavy chain V region (or V and C regions) can be cotransfected with analogous vectors carrying a light chain V region (or V and C regions), allowing for the expression of noncovalently associated Fvs (or complete antibody molecules).

CDR Exchange in a Synthetic Gene

The synthetic gene coding for mouse $V_H$ and $V_L$ 26-10 shown in FIGS. 4A and 4B were designed from the known amino acid sequence of the protein with the aid of Compugene, a software program. These genes, although coding for the native amino acid sequences, also contain non-native and often unique restriction sites flanking nucleic acid sequences encoding CDR's to facilitate CDR replacement as noted above.

Both the 3' and 5' ends of the large synthetic oligomers were designed to include 6-base restriction sites, present in the genes and the pUC vector. Furthermore, those restriction sites in the synthetic genes which were only suited for assembly but not for cloning the pUC were extended by "helper" cloning sites with matching sites in pUC.

Cloning of the synthetic DNA and later assembly of the gene was facilitated by the spacing of unique restriction sites along the gene. This allows corrections and modifications by cassette mutagenesis at any location. Among them are alterations near the 5' or 3' ends of the gene as needed for the adaptation to different expression vectors. For example, a PstI site is positioned near the 5' end of the $V_H$ gene. Synthetic linkers can be attached easily between this site and a restriction site in the expression plasmid. These genes were synthesized by assembling oligonucleotides as described above using a Biosearch Model 8600 DNA Synthesizer. They were ligated to vector pUC8 for transformation of *E. coli*.

Specific CDRs may be cleaved from the synthetic $V_H$ gene by digestion with the following pairs of restriction endonucleases: HPHI and BstXI for $CDR_1$; XbaI and DraI for $CDR_2$; and BanII and BanI for $CDR_3$. After removal of one CDR, another CDR of desired specificity may be ligated directly into the restricted gene, in its place if the 3' and 5' ends of the restricted gene and the new CDR contain complementary single stranded DNA sequences.

In the present example, the three CDRs of each of mouse $V_H$ 26-10 and $V_L$ 26-10 were replaced with the corresponding CDRs of glp-4. The nucleic acid sequences and corresponding amino acid sequences of the chimeric $V_H$ and $V_L$ genes encoding the FRs of 26-10 and CDRs of glp-4 are shown in FIGS. 4C and 4D. The positions of the restriction endonuclease cleavage sites are noted with their standard abbreviations. CDR sequences are underlined as are the restriction endonucleases of choice useful for further CDR replacement.

These genes were cloned into pUC8, a shuttle plasmid. To retain unique restriction sites after cloning, the $V_H$-like gene was spliced into the EcoRI and HindIII or BamHI sites of the plasmid.

Direct expression of the genes may be achieved in *E. coli*. Alternatively, the gene may be expressed in *E. coli* as a fusion product by splicing it into the host gene whose expression is regulated by interaction of a repressor with the respective operator. The protein can be induced by starvation in minimal medium and by chemical inducers. To date, the $V_H$ biosynthetic 26-10 gene has been expressed as such a fusion peptide behind the Trp and Tac promoters. The gene translation product must then be cleaved from the fusion protein by e.g., cyanogen bromide degradation, tryptic digestion, mild acid cleavage, and/or digestion with factor Xa protease. Therefore, a shuttle plasmid containing a synthetic gene encoding a leader peptide having a site for mild acid cleavage, and into which has been spliced the synthetic gene could be used for this purpose. In addition, synthetic DNA sequences encoding a signal peptide for secretion of the fusion protein into the periplasm of the host cell can also be incorporated into the plasmid.

After harvesting the gene product and optionally releasing it from a fusion peptide, its activity as an antibody binding site and its specificity for glp-4 (lysozyme) epitope are assayed by established immunological techniques, e.g., radioimmunoassay. Correct folding of the protein to yield the proper three-dimensional conformation of the antibody binding site is prerequisite for its activity. This occurs spontaneously in a host such as a myeloma cell which naturally expresses immunoglobulin proteins. Alternatively, for bacterial expression, the protein forms inclusion bodies which, after harvesting, must be subjected to a specific sequence of solvent conditions (e.g., diluted 20 ×from 8M urea 0.1M Tris-HCl pH9 into 0.15M NaCl, 0.01M sodium phosphate, pH 7.4 (Hochman et al., 1976 Biochem. 15:2706-2710) to assume its correct conformation and hence its active form.

FIGS. 4E and 4F show the DNA and amino acid sequence of chimeric V and $V_L$ comprising human FRs from NEWM and mouse CDRs from glp-4. The CDRs are underlined, as are restriction sites of choice for further CDR replacement or empirically determined refinement.

These constructs also constitute master framework genes, this time constructed of human framework sequences. They may be used to construct BABS of any desired specificity by appropriate CDR replacement.

Synthesis of a Single Chain Fv

A nucleic acid sequence encoding a composite Fv region or single chain antibody binding site was designed with the aid of Compugene, a computer program as described above. This gene contains nucleic acid sequences encoding the $V_H$ and $V_L$ regions of mouse 26-10 antibody linked together with a double-stranded synthetic oligonucleotide coding for a peptide with the amino acid sequence (Gly Gly Gly Gly Ser)$_3$ as shown in FIG. 6. This linker oligonucleotide contains helper cloning sites EcoRI and BamHI and was designed to contain the assembly sites SacI and AatII near its 5' and 3' ends, respectively. These sites enable match-up and ligation to the 3' and 5' ends of $V_H$ and $V_L$ 26-10, respectively, which also contain these sites ($V_H$-linker-$V_L$). However, the order of linkage to the oligonucleotide may be reversed ($V_L$-linker-$V_H$). Other restriction sites were designed into the gene to provide alternative assembly sites. A sequence encoding the FB fragment of protein A was used as a leader.

The gene fragments were synthesized using a Biosearch DNA Model 8600 Synthesizer as described above. Synthetic oligonucleotides were cloned according to established protocol described above using the pUC8 vector transfected into *E. coli*. The completed fused gene set forth in FIG. 6 was expressed in *E. Coli*.

After sonication, inclusion bodies were collected by centrifugation, and dissolved in 6M guanidine hydrochloride (GuHCl), 0.2M Tris, and 0.1M 2-mercaptoethanol (BME) pH 8.2. The protein was denatured and reduced in the solvent overnight at room temperature. Size exclusion chromatography was used to purify fusion protein from the inclusion bodies. A Sepharose 4B column (1.5×80 cm) was run in a solvent of 6M GuHCl and 0.01M NaOAc at pH 4.75. The protein solution was applied to the column at room temperature in 0.5-1.0 ml amounts. Fractions were collected and precipitated with cold ethanol. These were run on SDS gels, and fractions rich in the recombinant protein (approximately 34,000d) were pooled. This offers a simple first step for cleaning up inclusion body preparations without suffering significant proteolytic degradation.

For refolding, the protein was dialyzed against 100 ml of the same GuHCl-Tris-BME solution, and dialysate was diluted 11-fold over two days to 0.55M GuHCl, 0.02M Tris, and 0.01M BME. The dialysis sacks were then transferred to 0.01M NaCl, and the protein was dialyzed exhaustively before being assayed by RIA's for binding of I-125 labeled digoxin. The refolding procedure can be simplified by making a rapid dilution with water to reduce the GuHCl concentration to 1.1M, and then dialyzing against phosphate buffered saline (0.15M NaCl, 0.05M potassium phosphate, pH7, containing 0.03% NaN$_3$), so that it is free of any GuHCl within 12 hours. Product of both types of preparation showed binding activity.

All of the assays were conducted by a modification of the procedure of Mudgett-Hunter et al., (1982, J. Immunol. 129:1165-1172; 1985, Molec. Immunol. 22:477-488), so that they could be run on microtiter plates as a solid phase sandwich assay Binding data were collected using goat anti-mouse Fab antisera (gAmFab) as the primary antibody that initially coats the wells of the plate. These are polyclonal antisera which recognize epitopes that appear to reside mostly on mouse $V_L$. The samples of interest are next added to the coated wells and incubated with the gAmFab, which binds species that exhibit appropriate antigenic sites. After washing away unbound protein, the wells are exposed to I-125 labeled (radioiodinated) digoxin conjugates, either as I-125-dig-BSA or I-125-dig-lysine.

Figure 7:
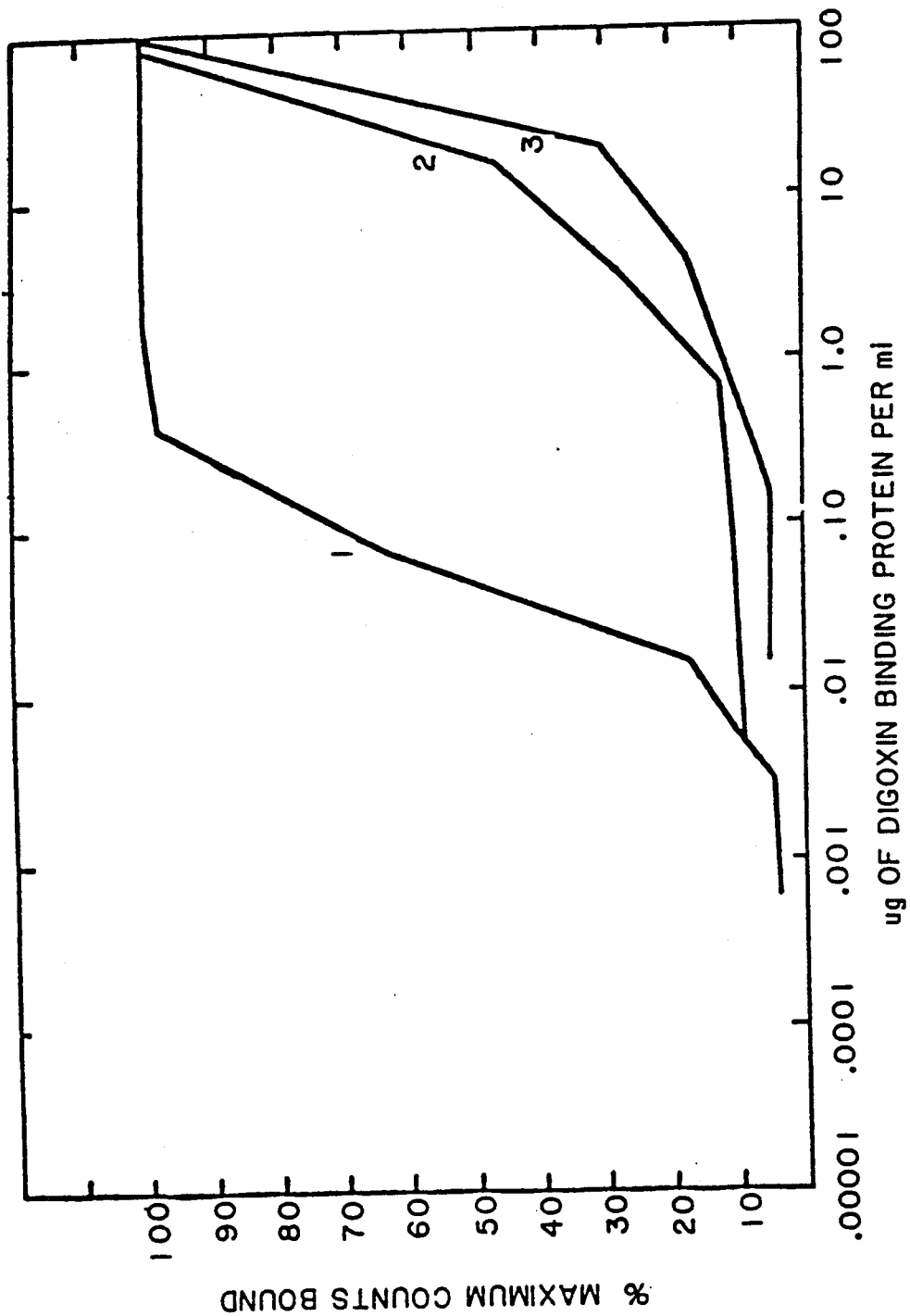
FIG. 7 is a graph of percent of undiluted units bound versus concentration comparing the binding of native 26-10 and the construct of FIG. 6 and FIG. 2A renatured using two different procedures Plot 3 represents the data for the native 26-10 antibody; plot 1 represents data from the construct of FIGS. 6 and 2A renatured using the slow folding procedures described herein; and plot 2 represents data from the same construct renatured using the fast dilution/quick folding procedure disclosed herein.

The data are plotted in FIG. 7, which shows the results of a dilution curve experiment in which the parent 26-10 antibody was included as a control. The sites were probed with I-125-dig-BSA in this assay. It was conducted as described above, with a series of dilutions prepared from initial stock solutions, including both the slowly refolded (1) and fast diluted/quickly refolded (2) single chain Fv proteins. The parallelism between all three dilution curves indicates that gAmFab binding regions on the BABS molecule are essentially the same as on the Fv of authentic 26-10 antibody, i.e., the surface epitopes appear to be the same for both proteins.

The sensitivity of these assays is such that binding affinity of the Fv for digoxin must be at least $10^6$. The parent 26-10 antibody has an affinity of $7 \times 10^9$ $M^{-1}$. Inhibition assays indicate the binding of I-125-digoxin-lysine may be as high as $10^8$, and can be inhibited by unlabeled digoxin, digoxigenin, digitoxin, digitoxigenin, gitoxin, acetyl strophanthidin, and ouabain in a way exactly parallel to the Parent 26-10 Fab. This demonstrates that the specificity of the biosynthetic protein is substantially identical to the original monoclonal.

The invention may be embodied in other specific forms without departing from the spirit and scope thereof. Accordingly, other embodiments are within the following claims.

What is claimed is:

1. A single polypeptide chain comprising:

two polypeptide domains connected by a polypeptide linker spanning the distance between the C-terminus of one domain to the N-terminus of the other and defining a single and complete site for binding a preselected antigen, wherein the amino acid sequence of one of said polypeptide domains comprises a heavy chain variable region, and the amino acid sequence of the other of said polypeptide domains comprises a light chain variable region, wherein at least one of said polypeptide domains comprises:

a recombinant polypeptide comprising:

a set of CDR amino acid sequences together defining a recognition site for said preselected antigen, wherein said CDR sequences are homologous to sequences obtained from a first immunoglobulin, a set of FR amino acid sequences linked to said set of CDR sequences, wherein said FR amino acid sequences are homologous to sequences obtained from a second immunoglobulin, said linked sets of CDR and FR amino acid sequences together defining a hybrid chimeric immunoglobulin variable region binding domain which is immonologically reactive with said preselected antigen; and a third amino acid sequence, peptide bonded to the N- or C- terminus of said site for binding, said third amino acid sequence comprising a single polypeptide chain having a conformation which confers biological activity to said third sequence under the same conditions that allow binding of said site for binding to said preselected antigen, said biological activity being independent of said site for binding.

2. The polypeptide chain of claim 1 wherein the FR sequences are of human origin.

3. A single chain recombinant protein comprising a first polypeptide region peptide bonded to at least one other polypeptide region, one of said regions being immunologically reactive with a preselected antigenic site and comprising two polypeptide domains with the C-terminus of one peptide bonded to the N-terminus of the other through a polypeptide linker, each of said domains comprising a set of CDR amino acid sequences interposed between a set of FR amino acid sequences, said sets of CDR and FR sequences in said domains together defining a binding site immunologically reactive with said preselected antigenic site, wherein the FR sequences are homologous with sequences obtained from a human immunoglobulin and the CDR sequences are non-human CDR sequences, another of said polypeptide regions being peptide bonded to the N- or C-terminus of said immunologically reactive binding site and comprising a single chain polypeptide having a conformation which confers biological activity to said another region under the same conditions that allow binding of said binding site region to said preselected antigenic site, said biological activity being independent of said binding site region.

4. The recombinant protein of claim 3 wherein the CDR sequences are of murine origin.

* * * * *